United States Patent [19]
Hensley et al.

[11] Patent Number: 5,840,838
[45] Date of Patent: Nov. 24, 1998

[54] PROCESS FOR ENHANCING THE ACTIVITY OF AMYLOID β PEPTIDES

[75] Inventors: Kenneth Hensley; D. Allan Butterfield; John M. Carney; Michael Aksenov, all of Lexington, Ky.

[73] Assignee: University of Kentucky Research Foundation, Lexington, Ky.

[21] Appl. No.: 609,090

[22] Filed: Feb. 29, 1996

[51] Int. Cl.$^6$ .............................. C07K 7/00; C07K 14/00
[52] U.S. Cl. ......................... 530/324; 530/326; 530/327; 530/328; 530/344
[58] Field of Search .................................... 530/324, 326, 530/327, 328, 344

[56] References Cited

U.S. PATENT DOCUMENTS

| | | | |
|---|---|---|---|
| 4,337,194 | 6/1982 | Diaz et al. ........................... | 260/112.5 |
| 4,530,784 | 7/1985 | Rosenberg .......................... | 260/112 R |
| 4,666,829 | 5/1987 | Glenner et al. ............................. | 435/6 |
| 4,966,963 | 10/1990 | Patroni .................................... | 530/351 |
| 5,144,006 | 9/1992 | Tam ........................................ | 530/345 |
| 5,213,962 | 5/1993 | Van Nostrand et al. ................. | 435/7.1 |
| 5,250,660 | 10/1993 | Shuman .................................. | 530/344 |

OTHER PUBLICATIONS

W. Bruce Rowe, et al., "Glutamine Synthetase (Sheep Brain)", 1951, pp. 900–910.
Richard E. Miller, et al., "Regulation of glutamine synthetase in cultured 3T3–L1 cells by insulin, hydrocortisone, and dibutyryl cyclic AMP", Jan. 9, 1978, pp. 1418–1422.
Waite et al., Neuro. Aging vol. 03 (1992) pp. 595–599.
Stricht et al., Eur. J. Biochem. vol. 233 (Oct. 1995) 293–298.
Hensley et al. Neuroreport vol. 6 No. 3 (Feb. 15, 1995) 489–492.

*Primary Examiner*—Cecilia J. Tsang
*Assistant Examiner*—Bennett Celsa
*Attorney, Agent, or Firm*—McDermott, Will & Emery

[57] ABSTRACT

A novel process for enhancing activity of an oligopeptide or polypeptide comprising the steps of: providing an oligopeptide or polypeptide, dissolving the oligopeptide or polypeptide in an organic solvent, heating, removing the solvent, and recovering an oligopeptide or polypeptide with enhanced activity is disclosed. Also disclosed are novel oligopeptides and polypeptides enhanced by the process according the invention.

11 Claims, 6 Drawing Sheets

PROCESS FOR ENHANCING THE ACTIVITY OF AMYLOID β PEPTIDES

This invention was made with Government support under Grant No. AG-10836 awarded by the National Institute of Health. The Government may have certain rights in this invention.

FIELD OF THE INVENTION

This invention relates to a novel process for enhancing activity of an oligopeptide or polypeptide comprising the steps of: providing an oligopeptide or polypeptide, dissolving the oligopeptide or polypeptide in an organic solvent, heating, removing the solvent, and recovering an oligopeptide or polypeptide with enhanced activity. The present invention also provides novel oligopeptides and polypeptides enhanced by the process according the invention.

BACKGROUND

Amyloid β peptide is a 39-43 residue peptide which is a proteolytic product of amyloid precursor protein. Amyloid β peptide comprises the 28 amino acids immediately amino-terminal to the single transmembrane domain of the precursor plus the first 11–15 residues of that domain. The amyloid β peptide contains both hydrophobic and hydrophilic domains. Amyloid plaques, a brain lesion diagnostic of Alzheimer's disease, are composed primarily of amyloid β peptide. Synthetic amyloid β peptides are toxic to central nervous system neurons in vitro. While the mechanism for this neurotoxicity is poorly understood, there have been reports that the neurotoxicity results from free radical production enhanced by the peptide.

Various processes for preparing and purifying biological materials are known in the art. For example, U.S. Pat. No. 4,966,963 to Patroni discloses a method for the preparation of a protein in a biologically active or native form, which method includes (1) providing a source of protein in a solubilized form and an agent capable of rupturing atomic forces within the molecule, and (2) contacting the protein with the atomic forces rupturing agent in an amount sufficient to allow the protein to convert to physiologically active form. The patent discloses that protein aggregates which may be recovered are selected from protein precipitates including inclusion bodies and cytoplasmic aggregates.

U.S. Pat. No. 5,144,006 to Tam relates to a method for the oxidative folding of a peptide or protein substrate containing reactive sulfhydryl groups to form disulfide rings on bridges by reacting the substrate in an aqueous media with DMSO or other hydrocarbon sulfites. Other hydrocarbon sulfites include substituted hydrocarbons in which hydrogen is replaced with a reaction inert substituent such as hydroxy or halogen. These include symmetrical and non-symmetrical dialkyl sulfoxide containing up to six carbon atoms and further compounds in which the sulphur atom and the carbon atoms to which it is joined form a cyclic alkylene sulfoxide containing four or five carbon atoms.

U.S. Pat. No. 4,530,784 to Rosenberg relates to a method of extracting a biologically active factor that restores contact inhibition of growth to malignant cells in mammals by mixing a media conditioned by growth of a contact inhibited cell culture together with a volatile non-denaturing precipitating agent. The precipitate formed by this reaction is separated from the mixture and extracted with a biologically acceptable ionic buffering agent.

U.S. Pat. No. 4,337,194 to Diaz et al. relates to a process for the preparation of somatostatin wherein a step-wise peptide coupling reaction is affected in solution in DMF and the product of the reaction is isolated by evaporation of the DMF or by precipitation by addition of a second solvent which renders the somatostatin insoluble. Then, the obtained crude peptide is purified by solid phase washings with the aid of suitable solvents which dissolve the impurities.

U.S. Pat. No. 5,250,660 to Shuman relates to a process for the purification of peptides comprising chromatographing the impure salt of certain tripeptides via reversed phase high performance liquid chromatography by employing a gradient of about 2% to about 40% acetonitrile in an aqueous phase containing an inorganic acid corresponding to the salt form of the tripeptide at a pH between about 2 and about 3. Following the collection of the salt of the tripeptide in the eluate, the pH of the eluate is adjusted with water insoluble resin in basic form to between about pH 4 to about pH 6, filtering the resin and isolating the pure salt by removing the water from the filtrate.

U.S. Pat. No. 5,213,962 to Van Nostrand et al. relates to the purification, detection and methods of use of protease nexin-2 (PN-2) which is believed to be derived from the β-amyloid precursor protein. The patent discloses a method for purifying PN-2 employing a monoclonal antibody produced by Hybridoma Cell Line mAbP2-1 in an immunoaffinity step. In this method, pooled PN-2 containing fractions from a primary dextran sulphate-sepharose affinity step were directly applied to a mAbP2-1 monoclonal antibody immunoaffinity column. After washing, apparently homogenous PN-2 was eluted with low pH buffer. The overall activity yield from numerous purifications was between 70–85%.

U.S. Pat. No. 4,666,829 to Glenner et al. discloses a novel polypeptide which is used as a marker for Alzheimer's disease. The polypeptide can be used to obtain antibodies which will recognize antigenic determinants of the polypeptide or homologous polypeptides in tissues or body fluids and which may be used in a specific immunologic diagnostic test for Alzheimer's disease. Moreover, the polypeptide can be used to produce a nucleotide probe which can hybridize with the gene which codes for this or a homologous polypeptide. Such a probe can also be utilized in a specific diagnostic test for the disease.

U.S. Pat. No. 5,262,332 to Selkoe relates to a method for screening for Alzheimer's disease, comprising the steps of:

obtaining a skin tissue biopsy sample from a patient suspected of having Alzheimer's disease; performing an extraction suitable for extracting β-amyloid protein, or a β-amyloid precursor protein fragment comprising β-amyloid protein, from the biopsy sample, and thereby obtaining an extract sample; optionally additionally solubilizing the β-amyloid protein or the β-amyloid precursor protein fragment comprising β-amyloid protein present in the extract sample, and thereby obtaining a solution sample;

contacting the extract sample or the solution sample with a quantity of antibodies specific to β-amyloid protein or to a precursor protein fragment comprising β-amyloid protein or to a peptide fragment of β-amyloid protein of at least about eight amino acids sufficient to allow detection of said protein, protein fragment or peptide fragment; and, detecting the specific binding reaction in the extract or solution sample between the antibodies and the β-amyloid protein or the β-amyloid precursor protein fragment comprising β-amyloid protein wherein the presence of said binding reaction is indicative of Alzheimer's disease.

Many oligopeptides and polypeptides are necessary research tools for the study of pathways underlying various diseases. For example, synthetic amyloid B peptides are a necessary research tool for the study of the neurotoxicity that results from free radical production enhanced by the amyloid β peptide. Unfortunately, some oligopeptides and polypeptides such as synthetic amyloid β peptides demonstrate significant lot-to-lot variations in toxicity which is not attributed to contaminants or peptide impurities and which decreases their commercial value. More specifically, peptide reactivity greatly varies between synthetic lots due to structural factors. This variation is a major impediment because research cannot be accurately reproduced. None of the above-described processes and methods adequately address this problem. Thus, a long-felt need in the art exists for a process for treating oligopeptides and polypeptides such as synthetic amyloid B peptides, and other synthetic peptides, to create more uniformity in research applications. The present invention addresses this need.

SUMMARY OF THE INVENTION

It is accordingly one object of the present invention to provide a novel process for enhancing activity of an oligopeptide or polypeptide comprising the steps of: providing an oligopeptide or polypeptide, dissolving the oligopeptide or polypeptide in an organic solvent, heating, removing the solvent, and recovering an oligopeptide or polypeptide with enhanced activity.

Another object of the invention is to provide a novel process for enhancing activity of an oligopeptide or polypeptide wherein there is negligible sample loss.

A further object of the present invention is to provide novel oligopeptides and polypeptides enhanced by the process according the invention.

The above and other objects of the invention will become readily apparent to those of skill in the relevant art from the following detailed description, wherein only the preferred embodiments of the invention are shown and described, simply by way of illustration of the best mode of carrying out the invention. As is readily recognized, the invention is capable of modifications within the skill of the relevant art without departing from the spirit and scope of the invention.

DETAILED DESCRIPTION OF THE INVENTION

Figure 1:
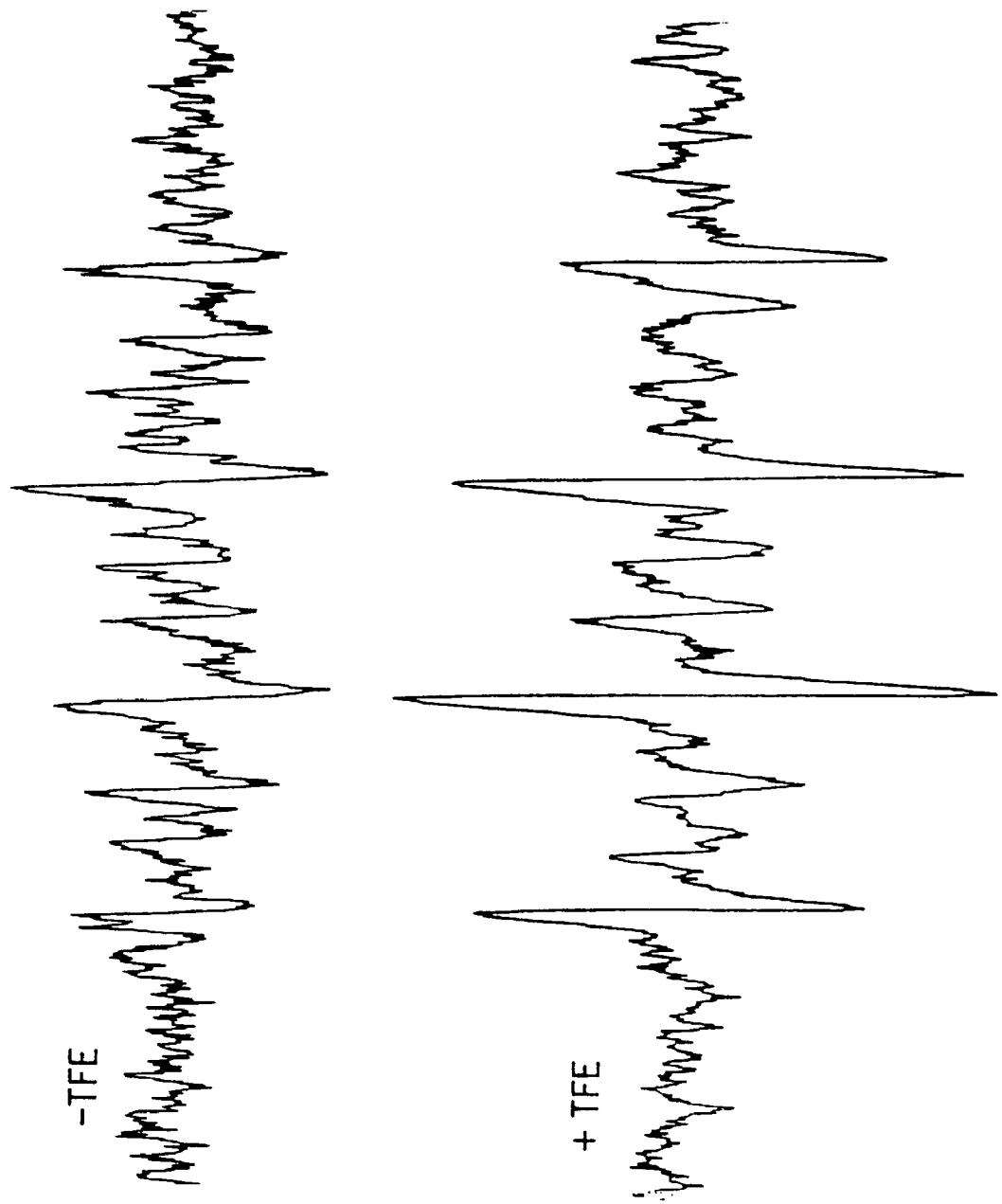
FIG. 1 shows the PBN spin adducts formed by co-incubation of Aβ(1-40) (SEQ ID NO:8) before and after the TFE-restructuring process.

The present invention provide a novel process for enhancing activity of an oligopeptide or polypeptide comprising the steps of: providing an oligopeptide or polypeptide, dissolving the oligopeptide or polypeptide in an organic solvent, heating, removing the solvent, and recovering an oligopeptide or polypeptide with enhanced activity. The invention is based, in part, on the inventors' surprising and unexpected discovery that the process increases the chemical reactivity, biological functioning and aggregational characteristics of oligopeptides and polypeptides.

The present invention is particularly applicable to biologically active structure dependent oligopeptides and polypeptides. These oligopeptides and polypeptides may be purified or unpurified, and natural or synthetic. These biologically active polypeptides and peptides include growth hormones, interferons, immunogens, lymphokines, amyloid beta peptides, substance P peptide, catalytic antibodies, enzymes, and fragments thereof. Examples of synthetic oligopeptides and polypeptides corresponding to the amyloid beta peptide include Aβ(1-15) (SEQ ID NO:1), Aβ(1-28) (SEQ ID NO:2), Aβ(1-30) (SEQ ID NO:3), Aβ(1-33) (SEQ ID NO:4), Aβ(25-35) (SEQ ID NO:5), Aβ(1-36) (SEQ ID NO:6), Aβ(1-39) (SEQ ID NO:7), Aβ(1-40) (SEQ ID NO:8), Aβ(1-42) (SEQ ID NO:9), Aβ(1-47) (SEQ ID NO:10), and Aβ(1-52) (SEQ ID NO:11).

The oligopeptide or polypeptide may be dissolved in any suitable structure forming organic solvent, that is, solvents which modulate protein secondary and higher order structure. Suitable structure forming solvents include trifluoroethanol, dimethyl sulfoxide, hexafluorocyclohexane, morpholino-propanesulfonic acid, dimethylformamide, and acetonitrile. In a preferred embodiment, the oligopeptide or polypeptide is pre-treated with the solvent.

Before pre-treatment of the oligopeptide or polypeptide with the solvent and/or before dissolving the oligopeptide or polypeptide in the solvent, the solvent may be deoxygenated by any suitable means, for example, by thoroughly degassing by $N_2$ sparge.

The oligopeptide or polypeptide is dissolved in the solvent to an appropriate concentration ranging from about 0.01 to 10 mg/ml, preferably from about 0.1 to 5 mg/ml, and more preferably from about 0.15 to 1.0 mg/ml.

Then, the dissolved oligopeptide or polypeptide is incubated, for example, in glass vials, for a period of time ranging from about 30 minutes to about 4 hours, preferably from about 45 minutes to 3 hours, more preferably from about 1 hour to about 2 hours.

During incubation the samples are gently heated to any suitable temperature. Preferably temperatures ranging from about 20° to about 65° C., more preferably from about 40° to about 45° C. are used.

The sample may be equilibrated to room temperature before removing the solvent or the solvent may be removed immediately. The solvent may be removed by any appropriate method, so long as the method is suitable for the solvent and oligopeptide or polypeptide. Preferred methods for removing the solvent include evaporative deposition, for example, under a stream of $N_2$ gas, and lyophilization. The duration of the solvent removal step is (rapid) about 5 minutes to about 10 minutes.

The present invention also provides novel oligopeptides and polypeptides enhanced by the process according the invention.

The following examples are merely illustrative of the present invention and they should not be considered as limiting the scope of the invention in any way, as these examples and other equivalents will become more apparent to those skilled in the art in light of the present disclosure.

EXAMPLE 1

Solvation Activation Process

Trifluoroethanol (TFE) (Aldrich Chemical, Milwaukee, Wis.) was initially thoroughly degassed by $N_2$ sparge.

Samples of synthetic amyloid beta peptide, Aβ(1-40) (SEQ ID NO:8) [Bachem lot ZM094], were divided into TFE-treated and control samples. TFE-treated samples were dissolved in deoxygenated TFE to a concentration of 0.15 mg/ml and incubated in glass vials for 2 hours at 40°–45° C. The TFE/Aβ solution was initially cloudy but became clear after about 1 hour at 40° C. The TFE/Aβ solutions were equilibrated to room temperature followed by removal of the TFE by rapid evaporation under a stream of $N_2$ gas.

EXAMPLE 2

Peptide Toxicity Assessed By Glutamine Synthetase Inactivation

Glutamine synthetase (GS) was assayed in brain cortical homogenate prepared from male mongolian gerbils (Tumblebrook Farms, W. Brookfield, Mass.). Amyloid beta peptide was tested for its ability to inactivate GS by first preincubating the peptide for 24 hours in phosphate buffer (1 mg/ml concentration, 5 mM $K_2HPO_4/KH_2PO_4$+5 mM NaCl pH 7.0) then co-incubating the peptide solution with brain cytosolic extract prepared from gerbil cortical homogenates (brain protein concentration in incubate=0.2 mg/ml, peptide concentration 1 mg/ml). After 3 hours incubation at 37° C. in phosphate buffer, aliquots of GS/peptide co-incubate were removed and assayed for GS activity by the calorimetric method of Rowe et al., Glutamine Synthetase, Methods Enzymol. 17 New York: Academic Press, 1970: 900–910; as modified by Miller et al., Proc. Natl. Acad. Sci. USA 75, 1418–1422 (1978) and corrected for nonspecific glutaminase activity by comparison in the presence and absence of ADP and arsenate.

Figure 3:
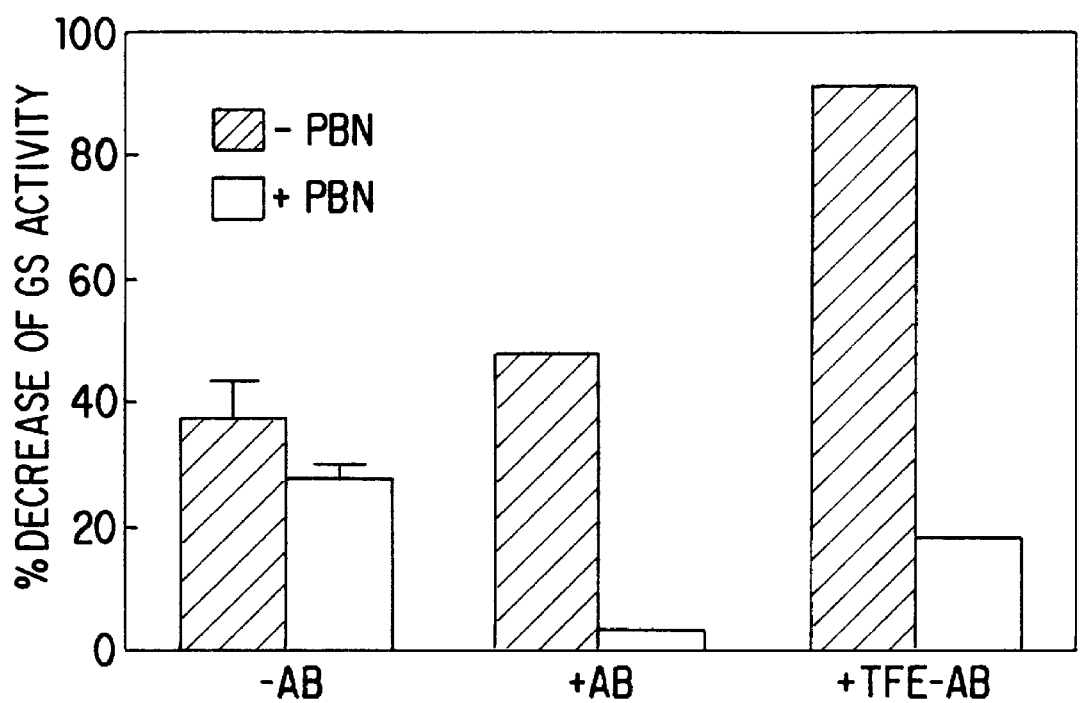
FIG. 3 shows the results of GS toxicity assays performed in parallel with, and using aliquots of the sample peptide preparations.
Figure 4A:
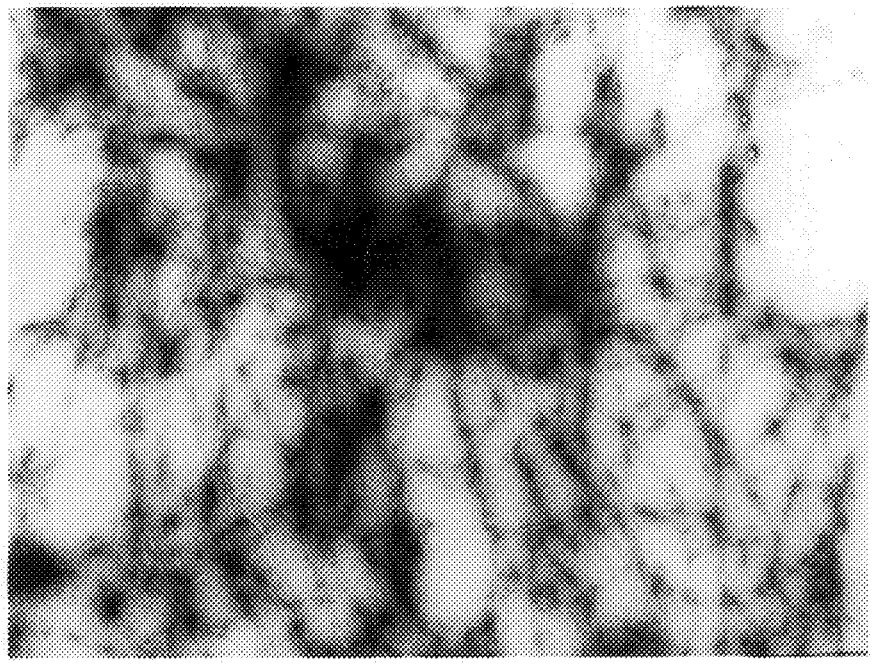
FIGS. 4A–4D show electron micrographs of Aβ(1-40) (SEQ ID NO:8) before and after TFE-SARP and incubated in PBS for 24 hours in the presence and absence of 50 mM PBN.
Figure 4B:
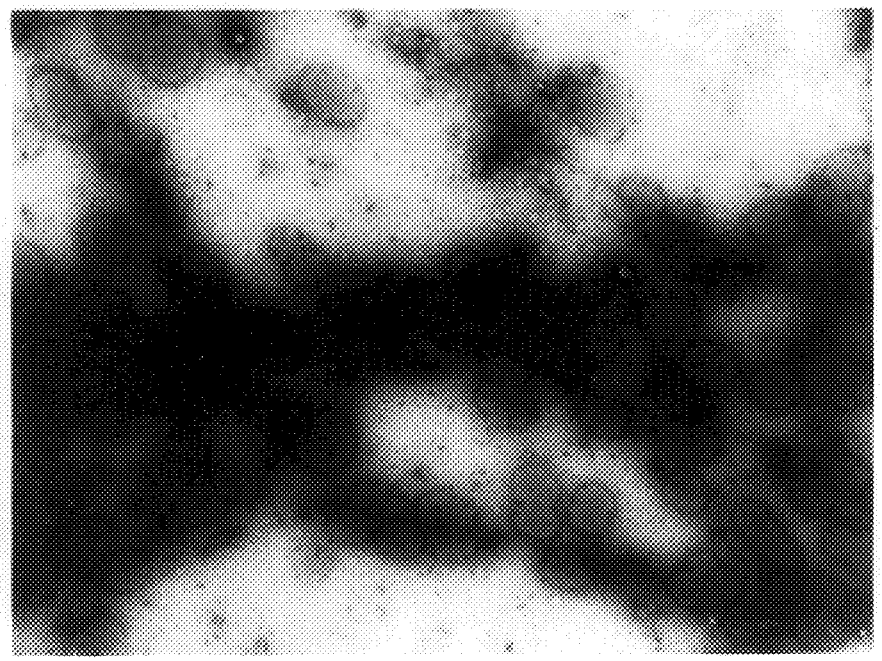
Figure 4C:
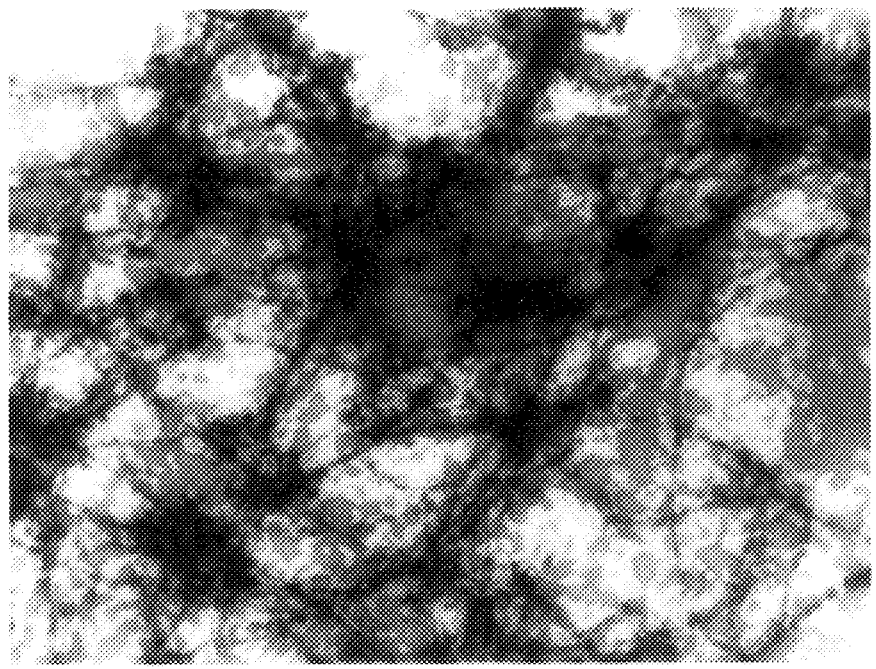
Figure 4D:

Toxic Aβ inactivates the oxidation-sensitive enzyme glutamine synthetase (GS) in vitro, and this measure of toxicity is used to index relative reactivity of Aβ samples. FIG. 3 illustrates the results of GS toxicity assays performed in parallel with, and using aliquots of the sample peptide preparations. The GS activity in this experiment is expressed relative to the initial GS activity of brain extract before incubation at 37° C., during which some GS activity is inevitably lost (even in the absence of added peptide) due to spontaneous oxidation of the sensitive enzyme. The activity of the enzyme decreases by approximately 30% after 3 hours incubation in the absence of Aβ. In the presence of unmodified Aβ(1-40) (SEQ ID NO:8) (Bachem lot ZM094), GS activity decreases approximately 45% relative to its initial activity. Thus, the peptide appears to have some toxic potential, but significantly less than has been previously reported with regard to the Aβ(1-40) (SEQ ID NO:8) or the toxic Aβ(25-35) (SEQ ID NO:5) sequences. TFE-treated Aβ(1-40) (SEQ ID NO:8) engenders a much greater loss in GS activity after 3 hours coincubation. These samples lost over 90% of initial GS activity. This represents a 3-fold increase in toxicity of the native, unmodified Aβ correlating with the EPR spin trapping results described herein.

In all cases, inclusion of 50 mM PBN in the GS incubate inhibited spontaneous GS oxidation and also Aβ-mediated loss in GS activity (FIG. 3). Between the PBN/Aβ-containing samples, GS activity showed a 3-fold greater decrease in the presence of TFE-pretreated Aβ than in the presence of native, unmodified Aβ, again in close correlation to EPR results obtained from these treatments.

EXAMPLE 3

Peptide Free Radical Generating Capacity

Amyloid beta free radical generation was assessed by electron paramagnetic resonance (EPR) spin trapping. Amyloid beta peptide (1 mg/ml) was incubated with phenyl-tert-butylnitrone [50 mM PBN (Centaur Pharmaceuticals, Sunnyvale, Calif.) in 5 mM $K_2HPO_4/KH_2PO_4$+5 mM NaCl pH 7.0] at 37° C. for 1–24 hours, then analyzed by EPR spectrometry using a Bruker 300 EPR spectrometer (incident power=19 mW, incident frequency=9.76 GHz, modulation amplitude=0.9 G, time constant=1.28 mS, conversiton time=10.28 mS).

Figure 2:
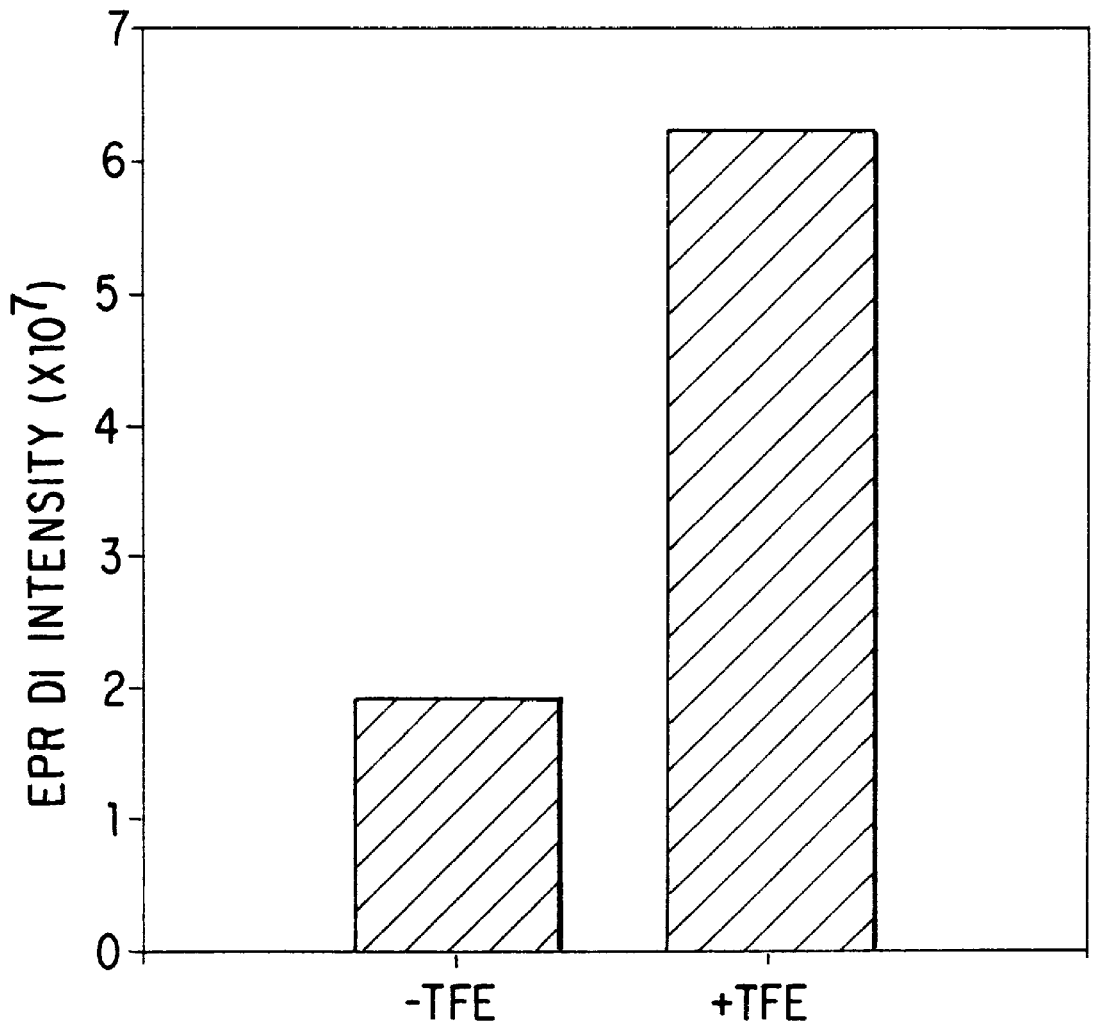
FIG. 2 shows that the yield of spin adduct was at least tripled after TFE treatment upon a double integration of the spectra.

Reactive amyloid beta produces stable free radical adducts of PBN which are detectable and quantifiable by EPR. The type and quantity of PBN adduct produced upon reaction with Aβ correlates with the degree of GS toxicity or cytotoxicity inherent in the Aβ sample. FIG. 1 shows the PEN spin adducts formed by conincubation of Aβ(1-40) (SEQ ID NO:8) [Bachem lot ZM094] before and after the TFE-restructuring process. Although, the spectra are quantitatively similar, the TFE-treated sample produced a significantly greater yield of spin-adduct and double integration of the spectra showed that the yield of spin adduct was at least tripled after TFE treatment (FIG. 2).

EXAMPLE 4

Peptide Aggregation Assessment by Electron Microscopy

Amyloid beta peptide was preincubated at 1 mg/ml for 24 hours at 37° C. in phosphate buffer ±50 mM PBN. 20 uL aliquots of the peptide incubate were evaporated to dryness on silicon grids and counterstained with uranyl acetate. Electron microscopy was performed on a Hitachi 7000 transmission electron microscope operating at 75 KV.

FIG. 4 shows electron micrographs of Aβ(1-40) (SEQ ID NO:8) before and after TFE-SARP and incubated in PBS for 24 hours in the presence and absence of 50 mM PBN. These also represent aliquots of samples used in the EPR and enzyme activity investigations. The native, unmodified Aβ formed visible fibrils upon incubation in the buffer. Native, unmodified Aβ coincubated with PBN demonstrated both fibrils and an amorphous component which stains more lightly and spans the interfibrillar regions. TFE-Aβ treatments differed dramatically in morphology from the native, unmodified peptide. TFE-treated Aβ formed very few fibrils, and along the fibril tracks were numerous circular or oblong deposits and regions of dark amorphous staining. In the presence of PBN, the fibril density appeared somewhat greater than in PBN absence; the circular components were smaller and sparcer; and lightly stained intrafibrillar material was seen in the PBN-coincubated, native Aβ samples.

EXAMPLE 5

Activation of Aβ(25-35) (SEQ ID NO:5)

The reactivity of low-activity Aβ(25-35) (SEQ ID NO:5) [Bachem lot WL650] was modified by TFE- and DMSO-treatment of the original peptide lyophilate. FIG. 5 shows the EPR spectra of PBN spin adducts formed from Aβ(25-25) (SEQ ID NO:5) before and after TFE- or DMSO-treatment. The TFE-treated peptide showed a qualitatively different reactivity than the native peptide, producing a 3-line EPR spectrum rather than a 4-line spectrum. Previous data showed a strong correlation between peptide toxicity and PBN spin adduct spectra, with 3-line generating peptides more toxic than 4-line generating variants. The DMSO-treated peptide demonstrated both the 4-line component and a nascent but weak 3-line component. Control experiments using $H_2O$ in place of the organic solvent had no effect on the nature of the PBN spin adduct.

EXAMPLE 6

Morphology of Aggregate Structures

Figure 5A:
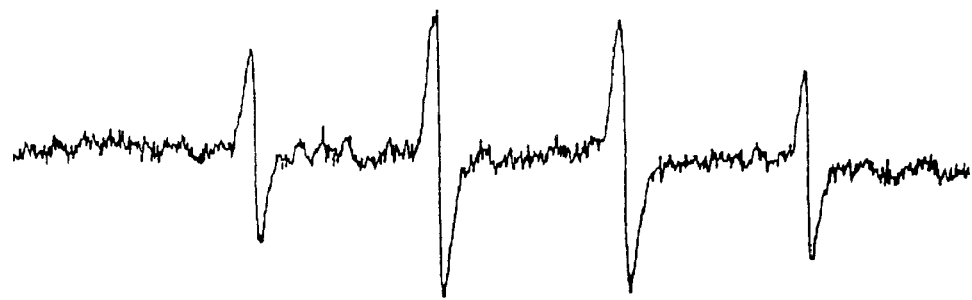
FIGS. 5A–5D show the EPR spectra of PBN spin adducts formed from Aβ(25-35) before and after TFE- or DMSO-treatment.
Figure 5B:
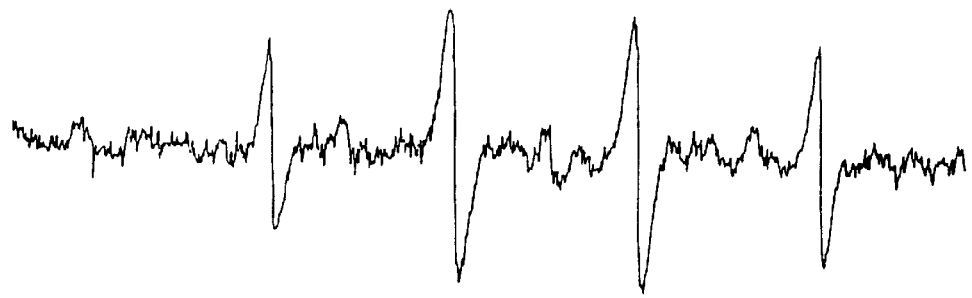
Figure 5C:
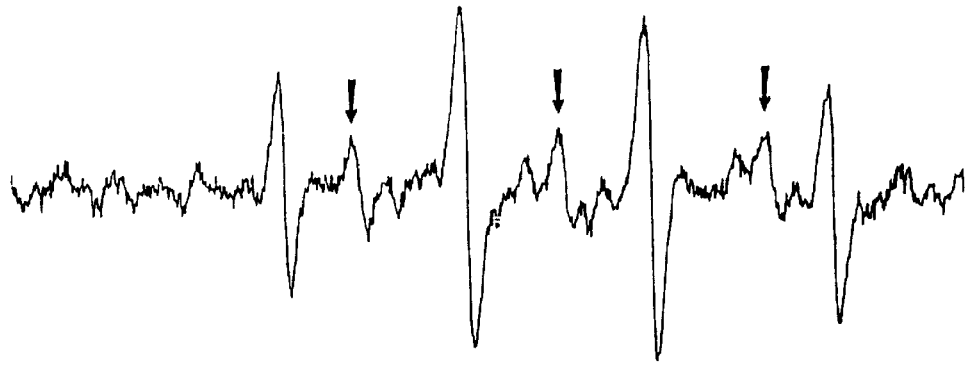
Figure 5D:
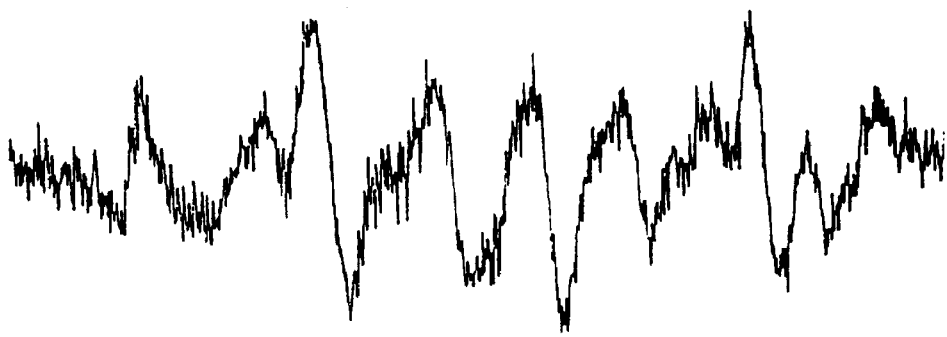

Toxic Aβ has a very facile fibril-forming capacity, whereas low-activity samples of Aβ form small amorphous or unstructured aggregates. The type of aggregate or polymer formed in the Aβ may reflect the initial aggregate condition of reactive polymolecular structures present in the peptide lyophilate prior to solubilization, and hence should be effected by protocols designed to modulate peptide structure and toxicity. FIG. 5 shows electron micrographic evidence that TFE treatment dramatically modified peptide fibrillogenic potential. The slightly toxic, native peptide formed a moderately dense network of filaments after 24 hours incubation in phosphate buffer (FIG. 5A). TFE-treated peptide formed only sparse fibrils, along which are located circular or spherical structures and opaquely-stained regions (FIG. 5B). This was the case in both PBN-free and PBN-coincubated, TFE-treated Aβ(1-40) (SEQ ID NO:8). In the PBN-treated samples, fibril density was slightly greater, and the spherical inclusions were smaller and fewer. In the PBN coincubated samples (both native and TFE-treated peptide), there were lightly stained deposits spanning the interfibrillar regions (FIG. 5 C,D). In control experiments where the PBN was added after the 24 hour peptide preincubation period (i.e., after fibrillogenesis), these highly stained deposits were not visible. Therefore, the lightly-stained PBN-derived structure represents a feature of PBN/Aβ interaction rather than simply a result of PBN precipitation.

EPR spectroscopy, enzyme assay, and electron microscopy have demonstrated a dramatic modification in reactivity of synthetic Aβ(1-40) (SEQ ID NO:8) upon treatment with the process of the present invention. The 3-fold increase in EPR signal intensity and GS inactivation upon TFE treatment, along with the observation that GS activity is protected by PBN inclusion, shows that the oxidative potential of the Aβ peptide is markedly increased by TFE-mediated unfolding and subsequent refolding of the peptide. The electron microscopic data clearly indicate a difference in aggregation behavior between native and TFE-treated Aβ.

While not wishing to be bound by any particular theory, it is possible that lot-to-lot variations in potency among synthetic Aβ peptides stem from alternate positioning of reactive radicalization sites within polymolecular aggregates of the peptide lyophilate. By separating and unfolding small polymolecular aggregates in the lyophilate and thereby freeing previously concealed reactive peptide radicalization sites, the present process significantly enhances the reactivity of synthetic peptides, including synthetic Aβ peptides.

DETAILED DESCRIPTION OF THE DRAWINGS

FIG. 1: PBN spin adduct EPR spectra obtained from synthetic Aβ(1-40) (SEQ ID NO:8) before (upper) and after (lower) TFE-treatment as described in the text;

FIG. 2: Double integrated intensity (arbitrary units) of EPR signals corresponding to TFE-treated or native Aβ(1-40) (SEQ ID NO.8) samples;

FIG. 3: GS inactivation by native and TFE-treated Aβ(1-40) (SEQ ID NO:8). Solid bars indicate samples of Aβ(1-40) (SEQ ID NO:8) incubated at 1 mg/ml for 24 hours at 37° C. in PBS pH 7.0; hollow bars indicate samples that also contained 50 mM PBN. After the 24 hour incubation period, the peptide samples were coincubated with brain extract (1 mg/ml peptide, 0.2 mg/ml brain extract) for 3 hours prior to GS assay. Data are represented as % loss of GS activity relative to GS samples that were not subjected to 3 hours of 37° C. incubation;

FIG. 4: Electron micrographs of Aβ(1-40) (SEQ ID NO:8) after 24 hours incubation in phosphate. A: Native, untreated peptide. B: TFE-treated peptide. C: Native peptide coincubated with 50 mM PBN. D: TFE-treated peptide coincubated with 50 mM PBN; and FIG. 5: PBN spin adduct EPR spectra obtained from synthetic Aβ(25-35) (SEQ ID NO:5) (lot WL650) treated by various solvation procedures prior to coincubation of peptide lyophilate with PBN. A: native, unmodified peptide. B: Peptide dissolved in $H_2O$ and relyophilized prior to spin trapping. C: Peptide dissolved in DMSO and relyophilized prior to spin trapping. Arrows indicate nascent 3-line component. D: Peptide dissolved in TFE and $N_2$ evaporated prior to spin trapping.

The purpose of the above description and examples is to illustrate some embodiments of the present invention without implying any limitation. It will be apparent to those of skill in the art that various modifications and variations may be made to the present invention without departing from the spirit or scope of the invention.

We claim:

1. A process for treating a synthetic amyloid beta peptide, which process comprising the steps of:
    a) providing a synthetic amyloid beta peptide;
    b) dissolving the synthetic amyloid beta peptide in a deoxygenated solvent selected from the group consisting of trifluoroethanol, dimethyl sulfoxide, hexafluorocyclohexane, morpholino-propanesulfonic acid, dimethylformamide, and acetonitrile to a concentration ranging from about 0.01 to about 10 mg/ml;
    c) incubating the dissolved synthetic amyloid beta peptide for about 30 minutes to about 4 hours at a temperature between about 20° C. to about 65° C.;
    d) removing the solvent by evaporative deposition in about 5 to about 10 minutes; and
    e) recovering the synthetic amyloid beta peptide obtained in step d.

2. The process of claim 1, wherein the peptide recovered in step e) produces a three-line or four-line EPR(electron paramagnetic resonance) spectrum upon reaction with PBN (phenyl-tert-butylnitrone) with an increased integrated intensity relative to the provided peptide.

3. The process of claim 1, wherein the peptide recovered in step e) leads to greater loss of GS(glutamine synthetase) activity than the provided peptide.

4. The process of claim 1, wherein the peptide recovered in step e) shows sparse fibrils along which are located circular or spherical structures and opaquely stained regions in an electron micrograph.

5. The process of claim 1, wherein the synthetic amyloid beta peptide is selected from group consisting of Aβ(1-15), Aβ(1-28), Aβ(1-30), Aβ(1-33), Aβ(25-35), Aβ(1-36), Aβ(1-39), Aβ(1-40), Aβ(1-42), Aβ(1-47), and Aβ(1-52).

6. The process of claim 1, wherein the deoxygenated solvent is deoxygenated by $N_2$ sparge.

7. The process of claim 1, wherein the synthetic amyloid beta is dissolved in the deoxygenated solvent to a concentration of about 0.1 to about 5 mg/ml.

8. The process of claim 7, wherein the synthetic amyloid beta peptide is dissolved in the deoxygenated solvent to a concentration of about 0.15 to about 1.0 mg/ml.

9. The process of claim 1, wherein the incubating step is carried out at a temperature between about 40° C. to about 45° C.

10. A process according to claim 1, wherein the incubating step is carried out for about 45 minutes to about 3 hours.

11. A process according to claim 10, wherein the incubating step is carried out for about 1 hour to about 2 hours.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Asp  Ala  Glu  Phe  Arg  His  Asp  Ser  Gly  Tyr  Glu  Val  His  His  Gln
 1                   5                        10                        15
```

( 2 ) INFORMATION FOR SEQ ID NO:2:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Asp Ala Glu Phe Arg His Asp Ser Gly Tyr Glu Val His His Gln Lys
 1               5                  10                     15
Leu Val Phe Phe Ala Glu Asp Val Gly Ser Asn Lys
                20                  25
```

( 2 ) INFORMATION FOR SEQ ID NO:3:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Asp Ala Glu Phe Arg His Asp Ser Gly Tyr Glu Val His His Gln Lys
 1               5                  10                     15
Leu Val Phe Phe Ala Glu Asp Val Gly Ser Asn Lys Gly Ala
                20                  25                  30
```

( 2 ) INFORMATION FOR SEQ ID NO:4:

( i ) SEQUENCE CHARACTERISTICS:
        ( A ) LENGTH: 33 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Asp Ala Glu Phe Arg His Asp Ser Gly Tyr Glu Val His His Gln Lys
 1               5                  10                     15
Leu Val Phe Phe Ala Glu Asp Val Gly Ser Asn Lys Gly Ala Ile Ile
                20                  25                  30
Gly
```

( 2 ) INFORMATION FOR SEQ ID NO:5:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
Gly Ser Asn Lys Gly Ala Ile Ile Gly Leu Met
 1               5                  10
```

( 2 ) INFORMATION FOR SEQ ID NO:6:

( i ) SEQUENCE CHARACTERISTICS:
        ( A ) LENGTH: 36 amino acids (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:6:

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
               20                  25                  30

Gly Leu Met Val
           35

(2) INFORMATION FOR SEQ ID NO:7:

(i) SEQUENCE CHARACTERISTICS:
         (A) LENGTH: 39 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:7:

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
               20                  25                  30

Gly Leu Met Val Gly Gly Val
           35

(2) INFORMATION FOR SEQ ID NO:8:

(i) SEQUENCE CHARACTERISTICS:
         (A) LENGTH: 40 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:8:

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
               20                  25                  30

Gly Leu Met Val Gly Gly Val Val
           35                  40

(2) INFORMATION FOR SEQ ID NO:9:

(i) SEQUENCE CHARACTERISTICS:
         (A) LENGTH: 42 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:9:

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
               20                  25                  30

```
        Gly  Leu  Met  Val  Gly  Gly  Val  Val  Ile  Ala
                  35                      40
```

( 2 ) INFORMATION FOR SEQ ID NO:10:

( i ) SEQUENCE CHARACTERISTICS:
        ( A ) LENGTH: 47 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

```
Asp  Ala  Glu  Phe  Arg  His  Asp  Ser  Gly  Tyr  Glu  Val  His  His  Gln  Lys
1                    5                       10                      15

Leu  Val  Phe  Phe  Ala  Glu  Asp  Val  Gly  Ser  Asn  Lys  Gly  Ala  Ile  Ile
               20                       25                      30

Gly  Leu  Met  Val  Gly  Gly  Val  Val  Ile  Ala  Thr  Val  Ile  Val  Ile
          35                      40                      45
```

( 2 ) INFORMATION FOR SEQ ID NO:11:

( i ) SEQUENCE CHARACTERISTICS:
        ( A ) LENGTH: 52 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

```
Asp  Ala  Glu  Phe  Arg  His  Asp  Ser  Gly  Tyr  Glu  Val  His  His  Gln  Lys
1                    5                       10                      15

Leu  Val  Phe  Phe  Ala  Glu  Asp  Val  Gly  Ser  Asn  Lys  Gly  Ala  Ile  Ile
               20                       25                      30

Gly  Leu  Met  Val  Gly  Gly  Val  Val  Ile  Ala  Thr  Val  Ile  Val  Ile  Thr
          35                      40                      45

Leu  Val  Met  Leu
          50
```